United States Patent
Kim et al.

(10) Patent No.: US 10,307,742 B2
(45) Date of Patent: Jun. 4, 2019

(54) BETA ZEOLITE CATALYST FOR PREPARATION OF MIXTURE OF BTEX (BENZENE, TOLUENE, ETHYLBENZENE, XYLENE) FROM POLY AROMATIC HYDROCARBONS AND PREPARATION METHOD THEREOF

(71) Applicant: KOREA RESEARCH INSTITUTE OF CHEMICAL TECHNOLOGY, Daejeon (KR)

(72) Inventors: Jeong-Rang Kim, Daejeon (KR); Soon Yong Jeong, Daejeon (KR); Chul Ung Kim, Daejeon (KR); Tae Wan Kim, Daejeon (KR); Youjin Lee, Chungcheongnam-do (KR); Eun Sang Kim, Gyeonggi-do (KR); Joo Wan Kim, Seoul (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/272,687

(22) Filed: Sep. 22, 2016

(65) Prior Publication Data

US 2017/0100710 A1    Apr. 13, 2017

(30) Foreign Application Priority Data

Oct. 7, 2015 (KR) ......................... 10-2015-0140961

(51) Int. Cl.
*B01J 27/188* (2006.01)
*B01J 29/78* (2006.01)
*C07C 4/06* (2006.01)
*C10G 45/64* (2006.01)

(52) U.S. Cl.
CPC ............. *B01J 29/7815* (2013.01); *C07C 4/06* (2013.01); *C10G 45/64* (2013.01); *C07C 2529/78* (2013.01); *C10G 2400/30* (2013.01); *Y02P 20/52* (2015.11)

(58) Field of Classification Search
CPC ............................... B01J 29/7815; C07C 4/06
USPC ...................................... 585/24, 476
See application file for complete search history.

(56) References Cited

U.S. PATENT DOCUMENTS

| | | | | |
|---|---|---|---|---|
| 5,290,429 A * | 3/1994 | Delaney | ................. | B01J 23/883 208/145 |
| 2009/0314683 A1* | 12/2009 | Matsushita | .............. | B01J 29/48 208/111.3 |
| 2010/0081856 A1* | 4/2010 | Butler | ....................... | C07C 2/66 585/467 |
| 2013/0210611 A1* | 8/2013 | Kim | ..................... | B01J 29/7215 502/66 |
| 2014/0024871 A1* | 1/2014 | Yanagawa | .............. | C10G 45/60 585/476 |

FOREIGN PATENT DOCUMENTS

| | | |
|---|---|---|
| CN | 102909049 A | 2/2013 |
| CN | 102909055 A | 2/2013 |
| KR | 1020120042059 A | 5/2012 |

OTHER PUBLICATIONS

English language abstract for KR 1020120042059 A (2012).
Park et al. "Hydro-conversion of 1-methyl naphthalene into (alkyl) benzenes over alumina-coated USY zeolite-supported NiMoS catalysts." Fuel 90.1 (2011): 182-189.
Kim et al. "Novel Ni2P/Zeolite Catalysts for Naphthalene Hydrocracking to BTX." Catalysis Communications 45 (2014): 133-138.
English Abstract for CN 102909049 A (2013).
English Abstract for CN 102909055 A (2013).

* cited by examiner

*Primary Examiner* — Philip Y Louie
*Assistant Examiner* — Aaron W Pierpont
(74) *Attorney, Agent, or Firm* — Caesar Rivise, PC

(57) ABSTRACT

A beta zeolite catalyst for the preparation of a BTEX (benzene, toluene, ethylbenzene, xylene) mixture from polyaromatic hydrocarbons and a preparation method of the same are disclosed. The beta zeolite catalyst demonstrates high conversion of polyaromatic hydrocarbons and high BTEX production yield by containing optimum contents of the group VIB metals and cocatalysts, so that it can be effectively used as a beta zeolite catalyst for the production of BTEX.

10 Claims, No Drawings

BETA ZEOLITE CATALYST FOR PREPARATION OF MIXTURE OF BTEX (BENZENE, TOLUENE, ETHYLBENZENE, XYLENE) FROM POLY AROMATIC HYDROCARBONS AND PREPARATION METHOD THEREOF

BACKGROUND OF THE INVENTION

1. Field of the Invention

The present invention relates to a beta zeolite catalyst for the preparation of a BTEX (benzene, toluene, ethylbenzene, xylene) mixture from polyaromatic hydrocarbons and a preparation method of the same.

2. Description of the Related Art

In coping with the continued high oil price and deepening environmental problems, it is important strategy to upgrade the lower value heavy oil fraction containing a high content of polyaromatic compounds to the higher value middle distillate including diesel and BTEX (benzene, toluene, ethylbenzene, xylene).

Hydrogenation process and hydrocracking process are the two most representative methods to treat the polyaromatic compounds included in heavy oil fractions. In such processes, if naphthalene, one of the most representative polyaromatic hydrocarbons, is taken as an example, it is converted into alkyl benzene like BTEX through a series of hydrogenolysis in the presence of a catalyst.

At this time, the usable catalyst is a zeolite catalyst containing metals. The said zeolite catalyst is a bifunctional catalyst, so that the combined characteristics of both the acid function obtained by the zeolite support and the metal function are shown.

Particularly, the characteristic of the acid catalyst included in a zeolite support is the ability to induce dehydrogenation, cracking, isomerization, and dealkylation, and the characteristic of the metal material is the ability to induce hydrogenation, hydrogenolysis, and isomerization.

The balance and harmony between the acid catalyst characteristic and the metal catalyst characteristic is important for the bifunctional catalyst to be fully functioning in order to prepare a middle distillate and BTEX from polyaromatic hydrocarbons. Therefore, it is essential to make optimization of choice of metal materials, supports, and metal load, etc.

As a support, silica-alumina, alumina, or various zeolites can be used. The zeolite herein can be selected from the group consisting of ZSM-5 zeolite having 10-ring structure, HY zeolite having 12-ring structure, and beta zeolite.

In particular, the said zeolite has the well-developed micropores and the catalyst based on such zeolite has been applied to various acid-catalyzed reactions due to the pore structure containing proper acid sites.

In the previous study about the catalytic conversion into BTEX, an aromatic compound being widely used as a basic material in the field of petrochemistry, alkylbenzenes were able to be produced with a high yield by hydrocracking 1-methylnaphthalene using $NiMo/Al_2O_3/USY$ (Ultra Stable Y zeolite) as a catalyst. According to the previous reports, $Ni_2P/Beta$ catalyst was efficient in producing alkylbenzenes with a high yield via naphthalene hydrogenolysis among $Ni_2P$ catalysts supported on various supports ($SiO_2$, ZSM-5, Beta, or USY) (see non-patent references 1 and 2).

The present inventors studied to prepare an efficient catalyst for the conversion of polyaromatic hydrocarbons into products containing BTEX, the basic oil resource in the field of petrochemistry, wherein the catalyst is precisely capable of upgrading the lower value heavy oil fraction containing a high content of polyaromatic compounds produced from petroleum. As a result, the present inventors confirmed that the beta zeolite catalyst of the invention displayed not only a high conversion of polyaromatic hydrocarbons but also a high BTEX production yield, and accordingly the inventors completed this invention by confirming that the beta zeolite catalyst of the present invention can be effectively used as a catalyst for the production of BTEX.

PRIOR ART REFERENCE

Non-Patent Reference

Joo-Il Park et al., Fuel, 90 (2011) 182-189
Yong-Su Kim et al., Catalysis Communications, 45 (2014) 133-138

SUMMARY OF THE INVENTION

It is an object of the present invention to provide a beta zeolite catalyst for the preparation of BTEX (benzene, toluene, ethylbenzene, xylene) from polyaromatic hydrocarbons.

It is another object of the present invention to provide a method for preparing the said beta zeolite catalyst.

It is also an object of the present invention to provide a method for preparing BTEX from polyaromatic hydrocarbons using the beta zeolite catalyst above.

It is further an object of the present invention to provide BTEX prepared by using the beta zeolite catalyst above.

To achieve the above objects, the present invention provides a beta zeolite catalyst for the preparation of BTEX (benzene, toluene, ethylbenzene, xylene) from polyaromatic hydrocarbons which comprises a beta zeolite, a group VIB metal, and one of cocatalysts selected from the group consisting of phosphorus (P), aluminum (Al), boron (B), silicon (Si), and arsenic (As).

The present invention also provides a method for preparing the beta zeolite catalyst above comprising the following steps:

calcinating a beta zeolite (step 1);

preparing a precursor solution by mixing a group VIB metal precursor and one of cocatalyst precursors selected from the group consisting of P, Al, B, Si, and As (step 2);

impregnating the precursor solution prepared in step 2 in the beta zeolite calcinated in step 1 (step 3); and preparing a beta zeolite catalyst by drying and calcinating the beta zeolite impregnated in step 3 (step 4).

In addition, the present invention provides a method for preparing BTEX from polyaromatic hydrocarbons using the beta zeolite catalyst above.

The present invention further provides the BTEX prepared by using the said beta zeolite catalyst.

Advantageous Effect

The beta zeolite catalyst of the present invention is composed of the optimum contents of a group VIB metal and a cocatalyst for the beta zeolite, so that it displays not only the high conversion of polyaromatic hydrocarbons but also the high yield of BTEX, suggesting that the catalyst of the present invention can be effectively used as a beta zeolite catalyst for the preparation of BTEX.

DESCRIPTION OF THE PREFERRED EMBODIMENTS

Hereinafter, the present invention is described in detail.

The present invention provides a beta zeolite catalyst for the preparation of BTEX (benzene, toluene, ethylbenzene, xylene) from polyaromatic hydrocarbons which comprises a beta zeolite, a group VIB metal, and one of cocatalysts selected from the group consisting of P, Al, B, Si, and As.

At this time, the polyaromatic hydrocarbon can be $C_{10-14}$ polyaromatic hydrocarbon, but not always limited thereto. Preferably, the $C_{10-14}$ polyaromatic hydrocarbon can be non-substituted or substituted with one or more straight or branched $C_{1-5}$ alkyl. More preferably, the $C_{10-14}$ polyaromatic hydrocarbon herein can be selected from the group consisting of naphthalene, 1-methylnaphthalene, 2-methylnaphthalene, 2,4-dimethylnaphthalene, 1,3-dimethylnaphthalene, 1,6-dimethylnaphthalene, 2,6-dimethylnaphthalene, anthracene, 1-methylanthracene, 2-methylanthracene, phenanthrene, 1-methylphenanthrene, and 2-methylphenanthrene.

Hereinafter, the beta zeolite catalyst for the preparation of BTEX of the invention is described in more detail.

In general, a catalyst containing zeolite wherein a metal composition is impregnated displays the bi-functional characteristics. That is, the characteristics of an acid catalyst included in a zeolite support and the characteristics of a metal ingredient impregnated therein are both shown. The characteristics of an acid catalyst are exemplified by dehydrogenation, cracking, isomerization, and dealkylation, and the characteristics of a metal ingredient are exemplified by hydrogenation, hydrogenolysis, and isomerization.

To prepare BTEX from polyaromatic hydrocarbons, the present invention provides a beta zeolite catalyst wherein a group VIB metal is impregnated as a metal composition; a beta zeolite is used as a support; and as a cocatalyst to increase the catalytic activity, one of cocatalysts selected from the group consisting of P, Al, B, Si, and As is additionally impregnated therein.

First, the beta zeolite of the beta zeolite catalyst for the preparation of BTEX of the invention is described in more detail.

The beta zeolite generally provides the cracking function necessary for the selective ring-opening for the preparation of BTEX from polyaromatic hydrocarbons.

To provide the cracking function, the molar ratio of $SiO_2$ to $Al_2O_3$ in the beta zeolite is preferably 25-60:1. If the molar ratio of $SiO_2$ to $Al_2O_3$ is less than 25:1, the cracking activity to decompose the product is excessively induced, so that the selective ring-opening is inhibited because of the excess ring-opening caused instead. If the molar ratio of $SiO_2$ to $Al_2O_3$ is more than 60:1, acid sites are too weak and accordingly reactivity at the acid sites is too low, so that the acid catalyst cannot be fully functioning and therefore ring-opening is not induced, suggesting that successful preparation of BTEX is in question.

The beta zeolite of the present invention is a support having the 12-ring structure with comparatively big micropores and displaying the activity of an acid catalyst. When a reactant is introduced in the porous structure of the beta zeolite, the reactant is easily transferred at the active site, suggesting that the production of a side-product can be inhibited.

Next, the group VIB metal used for the beta zeolite catalyst for the preparation of BTEX of the invention is described in more detail.

The said group VIB metal provides such functions as hydrogenation, hydrogenolysis, and isomerization necessary for the selective ring-opening needed in the preparation of BTEX from polyaromatic hydrocarbons.

To provide the said catalytic functions, a group VIB metal is preferably included at the concentration of 0.60-1.80 mmol in 1 g of beta zeolite, and more preferably impregnated therein at the concentration of 0.70-1.50 mmol. If the group VIB metal is impregnated in 1 g of zeolite at the concentration of less than 0.60 mmol, the catalytic activity is reduced. On the other hand, if the concentration of the impregnated VIB metal is more than 1.80 mmol, acid sites of the beta zeolite are covered to reduce the reaction activity so that the characteristics of an acid catalyst is not fully displayed and accordingly ring-opening is not induced successfully, resulting in the failure of the expected BTEX production.

The group VIB metal of the invention exists in the form of a sulfide. The group VIB metal exists in the form of a metal oxide in the beta zeolite catalyst. At this time, the metal oxide does not have hydrogenation activity. So, when the metal oxide is sulfidated, hydrogenation activity with a proper strength is generated therein, suggesting that the material is now ready to be used as a catalyst for hydrogenation and at the same time becomes resistant against deactivation caused by sulfur and nitrogen oxide included in the reactant raw materials.

Further, the group VIB metal herein is exemplified by tungsten (W) or molybdenum (Mo), but not always limited thereto and tungsten (W) is more preferred herein.

The yield of BTEX according to the group VIB metal concentration was evaluated. As a result, when 1.10 mmol of the group VIB metal was impregnated in 1 g of beta zeolite, the conversion of polyaromatic hydrocarbons was high and the highest BTEX yield was obtained (see Experimental Example 1 and Table 1).

The concentration of the group VIB metal has to be adjusted in order for the metal to be functioning as a metal catalyst. So, as described above, the preferable concentration of the group VIB metal is suggested as 0.60-1.80 mmol, with which not only the polyhydrocarbon conversion is high but also the BTEX yield is guaranteed high.

Further, the cocatalyst selected from the group consisting of phosphorus (P), aluminum (Al), boron (B), silicon (Si), and arsenic (As), which was used for the beta zeolite catalyst for the preparation of BTEX of the invention, is described in more detail.

In general, the cocatalyst has the effect to increase the dispersion of the group VIB metal sulfide of the invention in a beta zeolite support, and to increase acidity of an acid catalyst.

To be functioning efficiently, the cocatalyst selected from the group consisting of phosphorus (P), aluminum (Al), boron (B), silicon (Si), and arsenic (As) is included preferably at the concentration of 0.10-0.50 mmol in 1 g of beta zeolite. If the concentration is less than 0.10 mmol, the function as a cocatalyst is very weak so that the reaction is not much improved. If the concentration is more than 0.50 mmol, the catalyst interrupts the active site of the group VIB metal sulfide, resulting in the decrease of reaction activity.

The cocatalyst herein is selected from the group consisting of phosphorus (P), aluminum (Al), boron (B), silicon (Si), and arsenic (As), but not always limited thereto. However, phosphorus (P) or aluminum (Al) is more preferred herein.

The yield of BTEX according to the cocatalyst concentration was evaluated. As a result, when 0.37 or 0.18 mmol of the cocatalyst was impregnated in 1 g of beta zeolite, the conversion of polyaromatic hydrocarbons was high and the highest BTEX yield was obtained (see Experimental Example 1 and Table 1).

The concentration of phosphorus (P) or aluminum (Al), as a cocatalyst, is preferably adjusted in order for the cocatalyst to be efficiently functioning. As explained hereinbefore, the content of a cocatalyst is preferably determined to be 0.10-0.50 mmol in order to increase not only the hydrocarbon conversion but also the BTEX yield.

The present invention also provides a method for preparing the beta zeolite catalyst above comprising the following steps:

calcinating a beta zeolite (step 1);

preparing a precursor solution by mixing a group VIB metal precursor and one of cocatalyst precursors selected from the group consisting of phosphorus (P), aluminum (Al), boron (B), silicon (Si), and arsenic (As) (step 2);

impregnating the precursor solution prepared in step 2 in the beta zeolite calcinated in step 1 (step 3); and preparing a beta zeolite catalyst by drying and calcinating the beta zeolite impregnated in step 3 (step 4).

Hereinafter, the method for preparing the said beta zeolite catalyst of the invention is described in more detail.

In the method for preparing the beta zeolite catalyst of the invention, step 1 is to calcinate a beta zeolite.

Particularly, the calcinating in step 1 is performed in air atmosphere, but not always limited thereto. The calcination makes the conversion of ammonium cations ($NH_4^+$) in the beta zeolite to protons ($H^+$) and the elimination of impurities possible.

At this time, the molar ratio of $SiO_2:Al_2O_3$ in the beta zeolite is preferably 25-60:1.

In the method for preparing the beta zeolite catalyst of the invention, step 2 is to prepare a precursor solution by mixing a group VIB metal precursor with one of cocatalyst precursors selected from the group consisting of phosphorus (P), aluminum (Al), boron (B), silicon (Si), and arsenic (As) in distilled water.

Particularly, a group VIB metal can be tungsten or molybdenum, and tungsten is more preferred, but not always limited thereto. The said cocatalyst is preferably selected from the group consisting of phosphorus (P), aluminum (Al), boron (B), silicon (Si), and arsenic (As), and phosphorus (P) or aluminum (Al) is more preferred.

When tungsten is used as a group VIB metal, the tungsten precursor can be ammonium metatungstate hydrate or tungstic acid, but not always limited thereto. When molybdenum is used as a group VIB metal, the molybdenum precursor is preferably ammonium heptamolybdate or ammonium molybdate tetrahydrate, but not always limited thereto.

When the cocatalyst is phosphorus (P), the cocatalyst precursor is phosphoric acid, meta Phosphoric acid, or dibutyl phosphate, but not always limited thereto. When the cocatalyst is aluminum (Al), the cocatalyst precursor can be aluminum isopropoxide, aluminum hydroxide, or aluminum chloride hydrate, but not always limited thereto.

In the method for preparing the beta zeolite of the invention, step 3 is to dry the impregnated beta zeolite and calcinate the dried beta zeolite to prepare the beta zeolite catalyst.

Particularly, the beta zeolite prepared in step 1 is impregnated by the metal precursor mixed solution prepared in step 2, resulting in the mixed solution. The solvent is dried by solvent impregnation method to disperse the group VIB metal oxide in the zeolite microspores. As a result, the beta zeolite catalyst is prepared.

More particularly, the mixed solution was dried in a 100-150° C. oven for 5-10 hours, followed by calcination at 400-600° C. for 5-7 hours in air atmosphere.

At this time, if the calcination temperature is under 400° C., the activity of the group VIB metal is limited. If the calcination temperature is over 600° C., the structure of the beta zeolite is destroyed and accordingly the catalytic activity is reduced.

In the meantime, a step of sulfidation of the beta zeolite catalyst calcinated via heat-treatment in step 3 can be additionally included.

Particularly, the said sulfidation of the beta zeolite catalyst prepared in step 3 is preformed in the presence of hydrogen sulfide at 300-400° C., but not always limited thereto.

Through the said sulfidation, the group VIB metal oxide without hydrogenation activity in the beta zeolite catalyst is sulfidated to a group VIB metal sulfide, so that the metal obtains hydrogenation activity with a proper strength. As a result, the catalyst becomes a proper catalyst for hydrogenation and at the same time acquires a strong resistance against deactivation caused by sulfur and nitrogen oxide included in the reactant raw materials.

Therefore, the method for preparing the beta zeolite catalyst of the invention can additionally include a step of sulfidation.

The present invention provides a method for preparing BTEX from polyaromatic hydrocarbons using the beta zeolite catalyst above.

Particularly, the selective ring-opening of 1-methylnaphthalene, the representative polyaromatic hydrocarbon, can be performed using continuous fixed bed reaction system. BTEX can be prepared by using the beta zeolite catalyst of the invention above.

The continuous fixed bed reaction system above is functioning to supply 1-methylnaphthalene continuously to a catalyst in the fixed bed for the reaction. By this system, gas yield and BTEX yield can be calculated by measuring the amount and composition of the catalytic reaction product.

In addition, the present invention provides the BTEX prepared by using the said beta zeolite catalyst.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Beta Zeolite ($SiO_2/Al_2O_3$, Molar Ratio 38) Catalyst 1

The beta zeolite catalyst wherein tungsten (W) and phosphorus (W) were impregnated in beta zeolite ($SiO_2/Al_2O_3$, molar ratio 38) was prepared by the following method. Herein, the content of tungsten in 1 g of beta zeolite was 1.10 mmol and the content of phosphorus in 1 g of beta zeolite was 0.37 mmol.

Step 1: Calcination of Beta Zeolite ($SiO_2/Al_2O_3$ Molar Ratio 38)

Beta zeolite was calcinated at 550° C. for 6 hours in air atmosphere to convert ammonium cations ($NH_4^+$) to protons ($H^+$) and impurities were eliminated.

Step 2: Preparation of Precursor Mixed Solution

The tungsten (W) precursor, ammonium metatungstate hydrate (($NH_4$)$_6H_2W_{12}O_{40}$·x$H_2O$, W content: 66.5 weight %, 1.55 g) and the phosphorus (P) precursor, phosphoric acid solution (H$_3$PO$_4$ content: 85 weight %, 0.21 g) were dissolved in distilled water (200 ml), resulting in the precursor solution.

Step 3: Preparation of Beta Zeolite Catalyst 5 g of the beta zeolite calcinated in step 1 was added to the precursor solution prepared in step 2, which was mixed well at room temperature for 2 hours. The temperature of the mixed solution was raised to 55° C. and water solvent was completely eliminated by evaporation, followed by complete drying in a 120° C. oven for 8 hours. Calcination was performed at 380° C. for 2.5 hours and at 550° C. for 4.5 hours in air atmosphere to give the beta zeolite catalyst.

Step 4: Sulfidation of Beta Zeolite Catalyst

The beta zeolite catalyst prepared in step 3 proceeded to sulfidation at 350° C. for 3 hours in the presence of 10% H$_2$S/H$_2$ to activate the tungsten oxide without hydrogenation activity.

EXAMPLE 2

Preparation of Beta Zeolite (SiO$_2$/Al$_2$O$_3$=38) Catalyst 2

A beta zeolite catalyst was prepared by the same manner as described in Example 1 except that the content of phosphorus impregnated in 1 g of beta zeolite was 0.18 mmol.

EXAMPLE 3

Preparation of Beta Zeolite (SiO$_2$/Al$_2$O$_3$=38) Catalyst 3

A beta zeolite catalyst was prepared by the same manner as described in Example 1 except that aluminum (0.37 mmol in 1 g of beta zeolite) was used instead of phosphorus.

EXAMPLE 4

Preparation of Beta Zeolite (SiO$_2$/Al$_2$O$_3$=38) Catalyst 4

A beta zeolite catalyst was prepared by the same manner as described in Example 1 except that aluminum (0.18 mmol in 1 g of beta zeolite) was used instead of phosphorus.

COMPARATIVE EXAMPLE 1

Preparation of Beta Zeolite (SiO$_2$/Al$_2$O$_3$=38) Catalyst 1

A beta zeolite catalyst was prepared by the same manner as described in Example 1 except that only tungsten (1.10 mmol in 1 g of beta zeolite) without phosphorus was used.

COMPARATIVE EXAMPLE 2

Preparation of Beta Zeolite (SiO$_2$/Al$_2$O$_3$=38) Catalyst 2

A beta zeolite catalyst was prepared by the same manner as described in Example 1 except that only tungsten (0.50 mmol in 1 g of beta zeolite) without phosphorus was used.

COMPARATIVE EXAMPLE 3

Preparation of Beta Zeolite (SiO$_2$/Al$_2$O$_3$=38) Catalyst 3

A beta zeolite catalyst was prepared by the same manner as described in Example 1 except that only tungsten (2.00 mmol in 1 g of beta zeolite) without phosphorus was used.

COMPARATIVE EXAMPLE 4

Preparation of Beta Zeolite (SiO$_2$/Al$_2$O$_3$=38) Catalyst 4

A beta zeolite catalyst was prepared by the same manner as described in Example 1 except that tungsten (0.50 mmol in 1 g of beta zeolite) alone was used.

COMPARATIVE EXAMPLE 5

Preparation of Beta Zeolite (SiO$_2$/Al$_2$O$_3$=38) Catalyst 5

A beta zeolite catalyst was prepared by the same manner as described in Example 1 except that tungsten (2.00 mmol in 1 g of beta zeolite) alone was used.

COMPARATIVE EXAMPLE 6

Preparation of Beta Zeolite (SiO$_2$/Al$_2$O$_3$=38) Catalyst 6

A beta zeolite catalyst was prepared by the same manner as described in Example 1 except that the content of phosphorus impregnated in 1 g of beta zeolite was 0.08 mmol.

COMPARATIVE EXAMPLE 7

Preparation of Beta Zeolite (SiO$_2$/Al$_2$O$_3$=38) Catalyst 7

A beta zeolite catalyst was prepared by the same manner as described in Example 1 except that the content of phosphorus impregnated in 1 g of beta zeolite was 0.55 mmol.

COMPARATIVE EXAMPLE 8

Preparation of Beta Zeolite (SiO$_2$/Al$_2$O$_3$=38) Catalyst 8

A beta zeolite catalyst was prepared by the same manner as described in Example 1 except that the content of phosphorus impregnated in 1 g of beta zeolite was 0.73 mmol.

COMPARATIVE EXAMPLE 9

Preparation of Beta Zeolite (SiO$_2$/Al$_2$O$_3$=38) Catalyst 9

A beta zeolite catalyst was prepared by the same manner as described in Example 1 except that aluminum (0.08 mmol in 1 g of beta zeolite) was used instead of phosphorus.

COMPARATIVE EXAMPLE 10

Preparation of Beta Zeolite (SiO$_2$/Al$_2$O$_3$=38) Catalyst 10

A beta zeolite catalyst was prepared by the same manner as described in Example 1 except that aluminum (0.55 mmol in 1 g of beta zeolite) was used instead of phosphorus.

COMPARATIVE EXAMPLE 11

Preparation of Beta Zeolite (SiO$_2$/Al$_2$O$_3$=38) Catalyst 11

A beta zeolite catalyst was prepared by the same manner as described in Example 1 except that aluminum (0.73 mmol in 1 g of beta zeolite) was used instead of phosphorus.

EXPERIMENTAL EXAMPLE 1

Preparation of BTEX Using the Beta Zeolite Catalyst

To investigate the gas yield and the BTEX (benzene, toluene, ethylbenzene, xylene) yield through the selective ring-opening of 1-methylnaphthalene using the beta zeolite catalysts prepared in Examples 1-4 and Comparative Examples 1-11, the selective ring-opening of 1-methylnaphthalene was performed by using a continuous fixed bed reactor.

At this time, 1 g of the beta zeolite catalysts prepared in Examples 1-4 and Comparative Examples 1-11 were filled in ½" reactor, to which hydrogen was spilled at the flow rate of 100 SCCM, during which the pre-treatment was performed at 400° C. for 8 hours under normal pressure.

Upon completion of the pre-treatment, the reaction temperature was maintained at 400° C. but the reaction pressure was raised to 50 bar by using BPR (Back Pressure Regulator) and the hydrogen flow rate was raised to 175 SCCM. Liquid 1-methylnaphthalene (C$_{11}$H$_{10}$, 95%), the raw material of the reaction, was added at the flow rate of 0.037 ml/min by using a high-pressure piston pump for the selective ring-opening reaction.

At this time, the molar ratio of hydrogen to 1-methylnaphthalene was 30. The catalytic reaction product was cooled down at room temperature, followed by sampling every 2-3 hours for the quantitative analysis. The gas yield was calculated with the obtained result of the quantification by the following formula.

Gas Yield (weight %)=(1-methylnaphthalene flow amount−liquid product flow amount)/(1-methylnaphthalene flow amount)×100

The liquid reaction product obtained by the sampling above proceeded to qualitative analysis by using GC-MS (Gas Chromatography-Mass Spectrometry, Agilent 7890A-5975C) equipped with DB-5MS UI column (60 m, 0.25 mm, 0.25) to confirm the composition. The content of each component was investigated by quantitative analysis using FID (Flame ionization detector) of GC (Younglin 6100 GC) equipped with the same column.

In this invention, not only the conversion of 1-methylnaphthalene (1mNap) and the gas yield but also the yields of BTEX, selective ring-opening products such as (alkyl)benzene including BTEX, hydrogenation products such as decalin and (alkyl)tetralin, and middle distillates including light hydrocarbons, selective ring-opening products, and hydrogenation products, can be calculated by the GC analysis. And the conversion of 1-methylnaphthalene is the sum of all the yields of gas, middle distillates including BTEX, and other impurities (not shown).

1-methylnaphthalene was reacted by using the beta zeolite catalysts prepared in Examples 1-4 and Comparative Examples 1-11 for 12 hours. Then, the conversion of 1-methyl naphthalene, the gas yield, the BTEX yield, and the middle distillate yield were measured and shown in Table 1.

TABLE 1

| Catalyst | Tungsten, phosphorus, and aluminum contents (mmol/Beta zeolite 1 g) | | | 1-methylnaphthalene Conversion (weight %) | Yield (weight %) | | |
|---|---|---|---|---|---|---|---|
| | Tungsten (W) | Phosphorus (P) | Aluminum (Al) | | Gas | BTEX | Middle distillate |
| Example 1 | 1.10 | 0.37 | — | 97.0 | 31.4 | 39.0 | 56.6 |
| Example 2 | 1.10 | 0.18 | — | 97.7 | 39.2 | 38.8 | 52.0 |
| Example 3 | 1.10 | — | 0.37 | 97.5 | 34.9 | 36.9 | 52.1 |
| Example 4 | 1.10 | — | 0.18 | 97.4 | 40.8 | 35.6 | 51.6 |
| Comparative Example 1 | 1.10 | — | — | 97.0 | 44.1 | 30.0 | 45.0 |
| Comparative Example 2 | 0.50 | — | — | 95.6 | 37.7 | 22.8 | 38.9 |
| Comparative Example 3 | 2.00 | — | — | 94.6 | 29.6 | 22.9 | 40.4 |
| Comparative Example 4 | 0.50 | 0.37 | — | 95.2 | 32.5 | 29.3 | 50.6 |
| Comparative Example 5 | 2.00 | 0.37 | — | 94.4 | 25.5 | 20.3 | 50.8 |
| Comparative Example 6 | 1.10 | 0.08 | — | 96.8 | 42.9 | 31.6 | 48.8 |
| Comparative Example 7 | 1.10 | 0.55 | — | 89.7 | 21.0 | 25.5 | 41.9 |
| Comparative Example 8 | 1.10 | 0.73 | — | 89.3 | 21.1 | 22.7 | 38.9 |
| Comparative Example 9 | 1.10 | — | 0.08 | 96.2 | 43.6 | 29.1 | 50.4 |
| Comparative Example 10 | 1.10 | — | 0.55 | 90.1 | 30.5 | 25.1 | 45.8 |
| Comparative Example 11 | 1.10 | — | 0.73 | 89.9 | 25.7 | 20.3 | 40.7 |

The 1-methylnaphthalene conversion shown in table 1 above is the sum of the gas yield, the middle distillate yield, and the yield of other impurities (not shown) and at this time the middle distillate includes BTEX. So, the sum of those yields is consistent with the 1-methylnaphthalene conversion.

As shown in table 1 above, when the beta zeolite catalysts using phosphorus or aluminum as a cocatalyst (Examples 1-4) were used, the BTEX yield was at least 35%. On the other hand, when the beta zeolite catalyst was used without a cocatalyst (Comparative Example 1), the BTEX yield was 30.0%, suggesting that the beta zeolite catalyst of the invention increased the BTEX yield significantly.

When the cocatalyst content in the beta zeolite catalyst was same, the BTEX yield was more excellent when 1.10 mmol of tungsten was included in 1 g of beta zeolite.

In addition, when the tungsten content in the beta zeolite catalyst was same, the conversion and the BTEX yield were more excellent when 0.18 mmol or 0.37 mmol of a cocatalyst was included in 1 g of beta zeolite.

Therefore, the beta zeolite catalyst of the present invention contains the optimum concentrations of a group VIB metal and a cocatalyst, so that it can be effectively used as a beta zeolite catalyst for the preparation of BTEX due to the increased polyaromatic hydrocarbon conversion and BTEX yield.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A beta zeolite catalyst for preparing BTEX from polyaromatic hydrocarbons comprising 1-methylnaphthalene, which comprises a beta zeolite, tungsten, and one cocatalyst selected from the group consisting of phosphorus and aluminum, wherein a content of the tungsten is about 1.1 mmol in 1 g of the beta zeolite catalyst, and a content of the cocatalyst is 0.18-0.37 mmol in 1 g of the beta zeolite catalyst.

2. The beta zeolite catalyst for the preparation of BTEX from polyaromatic hydrocarbons according to claim 1, wherein the beta zeolite comprises $SiO_2$ and $Al_2O_3$ at a molar ratio of 25-60:1.

3. The beta zeolite catalyst for the preparation of BTEX from polyaromatic hydrocarbons according to claim 1, wherein the tungsten is included in a form of a sulfide.

4. A method for preparing the beta zeolite catalyst of claim 1 comprising the following steps:
calcinating a beta zeolite;
preparing a precursor solution by mixing a tungsten precursor and one cocatalyst precursor selected from the group consisting of a compound containing phosphorus and a compound containing aluminum;
impregnating the calcinated beta zeolite with the precursor solution to obtain an impregnated beta zeolite; and
drying and calcinating the impregnated beta zeolite to obtain the beta zeolite catalyst.

5. The method for preparing the beta zeolite catalyst according to claim 4, wherein the tungsten precursor is selected from the group consisting of ammonium metatungstate hydrate and tungstic acid.

6. The method for preparing the beta zeolite catalyst according to claim 4, wherein when the cocatalyst is phosphorus, the cocatalyst precursor is selected from the group consisting of phosphoric acid, meta phosphoric acid, and dibutyl phosphate.

7. The method for preparing the beta zeolite catalyst according to claim 4, wherein the beta zeolite catalyst is additionally treated by sulfidation.

8. A method for preparing BTEX from polyaromatic hydrocarbons comprising reacting polyaromatic hydrocarbons in a presence of the beta zeolite catalyst of claim 1 to produce said BTEX,
wherein the polyaromatic hydrocarbons comprise 1-methylnaphthalene.

9. The method for preparing BTEX from polyaromatic hydrocarbons according to claim 8, wherein reacting the polyaromatic hydrocarbons is performed at a temperature of 300-500° C.

10. The method for preparing BTEX from polyaromatic hydrocarbons according to claim 8, wherein reacting the polyaromatic hydrocarbons is accomplished by a selective ring-opening reaction.

* * * * *